(12) United States Patent
Qiu (10) Patent No.: US 11,147,314 B2
(45) Date of Patent: Oct. 19, 2021

(54) ATOMIZER AND ELECTRONIC CIGARETTE THEREOF

(71) Applicant: Joyetech Europe Holding GmbH, Zug (CH)

(72) Inventor: Weihua Qiu, Jiangsu (CN)

(73) Assignee: JOYETECH EUROPE HOLDING GMBH, Zug (CH)

(*) Notice: Subject to any disclaimer, the term of this patent is extended or adjusted under 35 U.S.C. 154(b) by 506 days.

(21) Appl. No.: 16/264,820

(22) Filed: Feb. 1, 2019

(65) Prior Publication Data

US 2019/0159524 A1 May 30, 2019

Related U.S. Application Data

(63) Continuation-in-part of application No. PCT/CN2017/096256, filed on Aug. 7, 2017.

(30) Foreign Application Priority Data

Aug. 9, 2016 (CN) .......................... 201610648214.9

(51) Int. Cl.
*A24F 47/00* (2020.01)
*A24F 40/485* (2020.01)
*A61M 15/06* (2006.01)
*A24F 1/32* (2006.01)
*A24F 7/02* (2006.01)
*A24F 15/015* (2020.01)
*A24F 40/10* (2020.01)

(52) U.S. Cl.
CPC .............. *A24F 40/485* (2020.01); *A24F 1/32* (2013.01); *A24F 7/02* (2013.01); *A61M 15/06* (2013.01); *A24F 15/015* (2020.01); *A24F 40/10* (2020.01)

(58) Field of Classification Search
CPC ......... A24F 40/42; A24F 40/46; A24F 40/485
See application file for complete search history.

(56) References Cited

U.S. PATENT DOCUMENTS

2010/0200008 A1 8/2010 Taieb
2017/0006923 A1* 1/2017 Li .......................... B67D 99/00

FOREIGN PATENT DOCUMENTS

| CN | 204444248 U | 7/2015 |
| CN | 204670379 U | 9/2015 |
| CN | 204907937 U | 12/2015 |
| CN | 105286090 A | 2/2016 |
| CN | 105286091 A | 2/2016 |

(Continued)

*Primary Examiner* — Eric Yaary
(74) *Attorney, Agent, or Firm* — Novick, Kim & Lee, PLLC; Allen Xue (57) ABSTRACT

An atomizer for an electronic cigarette includes a liquid storage assembly, an adjustment assembly detachably mounted at one end of the liquid storage assembly, and an atomizing assembly received in the liquid storage assembly. The atomizing assembly comprises an atomizing head and an atomizing sleeve sleeved on the outside of the atomizing head. The adjustment assembly is defined with an intake passage therein. The atomizing head includes an atomizing core, at least one air intake groove in communication with the intake passage is axially defined on the outer surface of the side wall of the atomizing core, an air intake hole communicating with an air intake groove is defined at a lower end of the bottom of each of the air intake groove.

16 Claims, 10 Drawing Sheets

(56) References Cited

FOREIGN PATENT DOCUMENTS

| | | |
|---|---|---|
| CN | 205180374 U | 4/2016 |
| CN | 205337613 U | 6/2016 |
| CN | 105747282 A | 7/2016 |
| CN | 105768236 A | 7/2016 |
| CN | 205358220 U | 7/2016 |
| CN | 105876871 A | 8/2016 |
| CN | 106136331 A | 11/2016 |
| CN | 205922899 U | 2/2017 |
| CN | 205962836 U | 2/2017 |

* cited by examiner

ATOMIZER AND ELECTRONIC CIGARETTE THEREOF

CROSS-REFERENCE TO RELATED APPLICATIONS

This application is a continuation-in-part of International Patent Application No. PCT/CN2017/096256, filed on Aug. 7, 2017, entitled "atomizer and electronic cigarette thereof", which claims priority to Chinese Patent Application No. CN201610648214.9, filed on Aug. 9, 2016. All of the aforementioned patent applications are hereby incorporated by reference in their entireties.

FIELD

The present disclosure relates to the technical field of electronic cigarette, in particular to an atomizer and an electronic cigarette thereof.

BACKGROUND

In the market, external gas enters the electronic cigarette through the bottom of the electronic cigarette, the air inlet is in communication with the liquid absorbing member in the atomizer of the electronic cigarette, and the air inlet is located at the bottom of the electronic cigarette and exposed to the air. When the cigarette liquid absorbed by the liquid absorbing member reaches saturation, the cigarette liquid easily leaks out from the air inlet, resulting in waste of cigarette liquid, and the cigarette liquid easily contaminates the air inlet.

SUMMARY

The object of the present disclosure is to provide an atomizer and an electronic cigarette thereof, which can prevent the leakage of the cigarette liquid and is convenient to operate.

An atomizer includes a liquid storage assembly, an adjustment assembly detachably mounted at one end of the liquid storage assembly, and an atomizing assembly received in the liquid storage assembly. The adjustment assembly is defined with an intake passage therein. The atomizing assembly comprises an atomizing head and an atomizing sleeve sleeved on the outside of the atomizing head. The atomizing head comprises an atomizing core. At least one air intake groove in communication with the intake passage is axially defined on the outer surface of the side wall of the atomizing core. An air intake hole communicating with a corresponding air intake groove is defined at a lower end of the bottom of each of the air intake groove. The air enters the air intake groove through the intake passage, and enters inside of the atomizing core through the air intake hole.

In one embodiment, the atomizing core is provided with a recess. Openings are defined on opposite sides of the recess. The atomizer further includes a liquid absorbing member and a heating element, the liquid absorbing member wraps the heating element or the heating element wraps the liquid absorbing member, the liquid absorbing member and the heating element are located in the recess.

In one embodiment, the atomizing core includes a core and an isolation member disposed at a lower end of the inner wall of the core. The recess is defined on the core. The isolation member protrudes in the axial direction to form a partition portion received in the opening on both sides of the recess. The lower end of the liquid absorbing member abuts against the partition portion.

In one embodiment, the adjustment assembly includes an upper cover, and a mouthpiece connector rotatably mounted on the upper cover. The upper cover is provided with at least one first air inlet hole, the mouthpiece connector is provided with at least one second air inlet hole corresponding to the first air inlet hole, the first air inlet hole is in communication with the intake passage; when the second air inlet hole is at least partially overlapped with the first air inlet hole by rotating the mouthpiece connector, the second air inlet hole is in communication with the intake passage through the first air inlet hole.

In one embodiment, the adjustment assembly further comprises an upper cover connector and a vent tube received in the upper cover connector. One end of the upper cover connector is detachably connected to the atomizing sleeve, and the other end of the upper cover connector is connected to the upper cover. One end of the vent tube is connected to and in communication with the mouthpiece connector, and the other end of the vent tube is in communication with the inside of the atomizing core.

In one embodiment, the atomizing assembly further includes a top cover mounted on the top end of the atomizing core, the top cover is a hollow structure having an opening at each of two ends, one end of the vent pipe away from the mouthpiece connector is received in the top cover.

In one embodiment, the cavity between the outer wall of the vent pipe and the inner wall of the upper cover connector forms the intake passage.

In one embodiment, the sidewall of the atomizing sleeve is provided with at least one liquid inlet hole, the liquid inlet hole can completely covered by the liquid absorbing member.

In one embodiment, the adjusting assembly further includes an upper cover inner ring sleeved on the upper cover connector and an adjusting member rotatably sleeved on the upper cover inner ring. A first liquid injection hole is defined on the upper cover inner ring, a second liquid injection hole is defined on the adjusting member corresponding to the first liquid injection hole, rotating the adjustment member can enable the second liquid injection hole communicate with the first liquid injection hole.

In one embodiment, the liquid storage assembly further includes a support housing, a casing sleeved on the support housing, a base assembly detachably disposed at the lower end of the support housing and the casing, and a fixing member opposite to the base assembly and detachably disposed at the upper end of the support housing and the casing. The fixing member is detachably connected to the upper cover inner ring.

In one embodiment, the cavity among the outer side wall of the upper cover connector, the outer side wall of the atomizing sleeve, the inner side wall of the upper cover inner ring and the inner side wall of the support housing forms a liquid storage chamber communicating with the first liquid injection hole. The cigarette liquid in the liquid storage chamber can pass through the liquid inlet hole of the atomizing sleeve into the liquid absorbing member.

In one embodiment, a space between the inner wall of the atomizing sleeve and the outer wall of the partition portion forms an auxiliary liquid inlet. The cigarette liquid in the liquid storage chamber can pass through the auxiliary liquid inlet into the liquid absorbing member.

An electronic cigarette includes any one of the above atomizer.

The beneficial effects of the device are:

(1) The air intake is defined on the side wall of the atomizing core to prevent the leakage of excess cigarette liquid from the air intake when the liquid absorbing member is saturated, thereby preventing the air intake from being contaminated, and the structure of the atomizer is simple, and easy to use.

(2) The cigarette liquid in the liquid storage chamber enters the liquid absorbing member through the bottom of the atomizing core. On the one hand, the cigarette liquid can be efficiently utilized; on the other hand, the cigarette liquid in the lower end of the liquid storage chamber is prevented from being repeatedly heated to generate harmful substance, which may affect the health of the user.

(3) The user can adjust the amount of intake air entering the inside of the electronic cigarette by rotating the mouthpiece connector at the upper end of the atomizer to adjust the overlapping area of the first air inlet hole and the second air inlet hole, and the adjustment operation is more convenient.

BRIEF DESCRIPTION OF THE DRAWINGS

FIG. 10 is another cross-sectional view of the atomizer of FIG. 1. (FIG. 8 overall rotation 90°)

The following table list various components and reference numerals thereof.

| | |
|---|---|
| Atomizer 100 | Liquid storage assembly 10 |
| Adjustment assembly 30 | Liquid storage chamber 11 |
| Casing 13 | Base 147 |
| Atomizing head 21 | Atomizing sleeve 22 |
| Intake passage 31 | Outlet passage 32 |
| Adjustment member 34 | Upper cover connector 35 |
| Upper cover 37 | Mouthpiece connector 38 |
| First through hole 142 | First sealing member 143 |
| Second sealing member 145 | First electrode 146 |
| First inner thread 153 | Atomizing core 211 |
| Heating member 213 | Liquid inlet hole 221 |
| First outer thread 331 | First liquid injection hole 332 |
| Fourth sealing member 334 | Second liquid injection hole 341 |
| Second outer thread 351 | Receiving groove 2121 |
| Lower connector 372 | First connecting member 373 |
| Connecting tube 382 | Second connecting member 383 |
| Air intake groove 2112 | Air intake 2113 |
| Base assembly 14 | First air inlet hole 3732 |
| Second electrode 25 | Auxiliary liquid inlet 2114 |
| Isolation member 2116 | Partition portion 2117 |
| Atomizing assembly 20 | Liquid absorbing member 212 |
| Support housing 12 | Second inner thread 222 |
| Fixing member 15 | Positioning groove 333 |
| Top cover 23 | Positioning block 342 |
| Upper cover inner ring 33 | Upper connector 371 |
| Vent tube 36 | Main body 381 |
| First annular groove 141 | Recess 2111 |
| Electrode sleeve 144 | Third sealing member 24 |
| Second annular groove 151 | Second air inlet hole 3831 |
| Core 2115 | Third through hole 3731 |

DETAILED DESCRIPTION OF PREFERRED EMBODIMENTS

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

Several definitions that apply throughout this disclosure will now be presented.

The term "coupled" is defined as connected, whether directly or indirectly through intervening components, and is not necessarily limited to physical connections. The connection can be such that the objects are permanently connected or releasably connected. The term "comprising," when utilized, means "including, but not necessarily limited to"; it specifically indicates open-ended inclusion or membership in the so-described combination, group, series and the like.

When a feature or element is herein referred to as being "on" another feature or element, it can be directly on the other feature or element or intervening features and/or elements may also be present.

Terminology used herein is for the purpose of describing particular embodiments only and is not intended to be limiting of the disclosure. As used herein, the term "and/or" includes any and all combinations of one or more of the associated listed items and may be abbreviated as "/".

Figure 1:
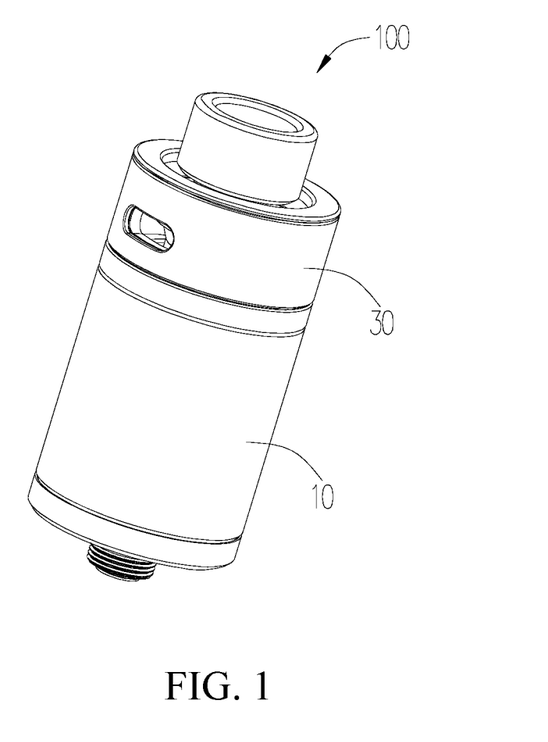
FIG. 1 is a perspective view of an atomizer according to a first embodiment of the present disclosure.
Figure 2:
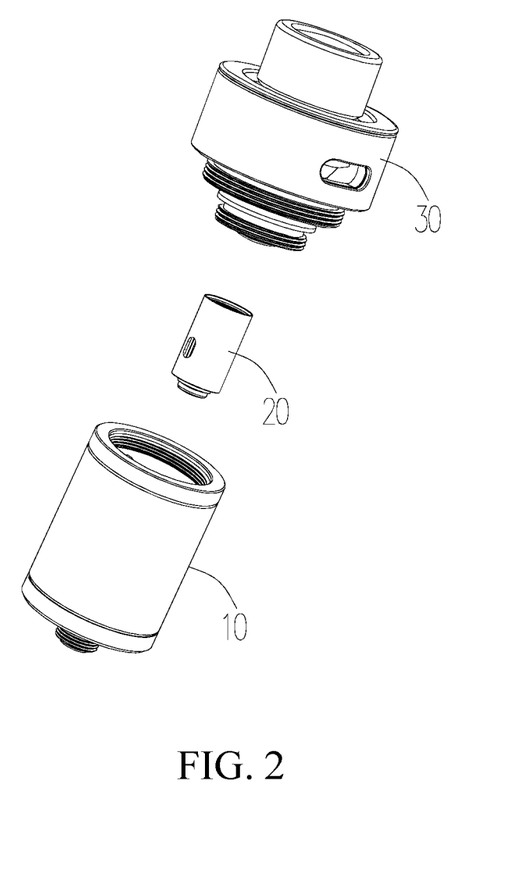
FIG. 2 is a partially exploded perspective view of the atomizer of FIG. 1.

Referring to FIG. 1 and FIG. 2, the present disclosure provides an electronic cigarette includes an atomizer 100 and a power supply device (not shown) connected to the atomizer 100, in one embodiment, the power supply device is disposed at a lower end of the atomizer 100. The atomizer 100 includes a liquid storage assembly 10, an atomizing assembly 20, and an adjustment assembly 30. The adjustment assembly 30 is detachably located at one end of the liquid storage assembly 10, and the atomizing assembly 20 is received in the liquid storage assembly 10.

Figure 3:
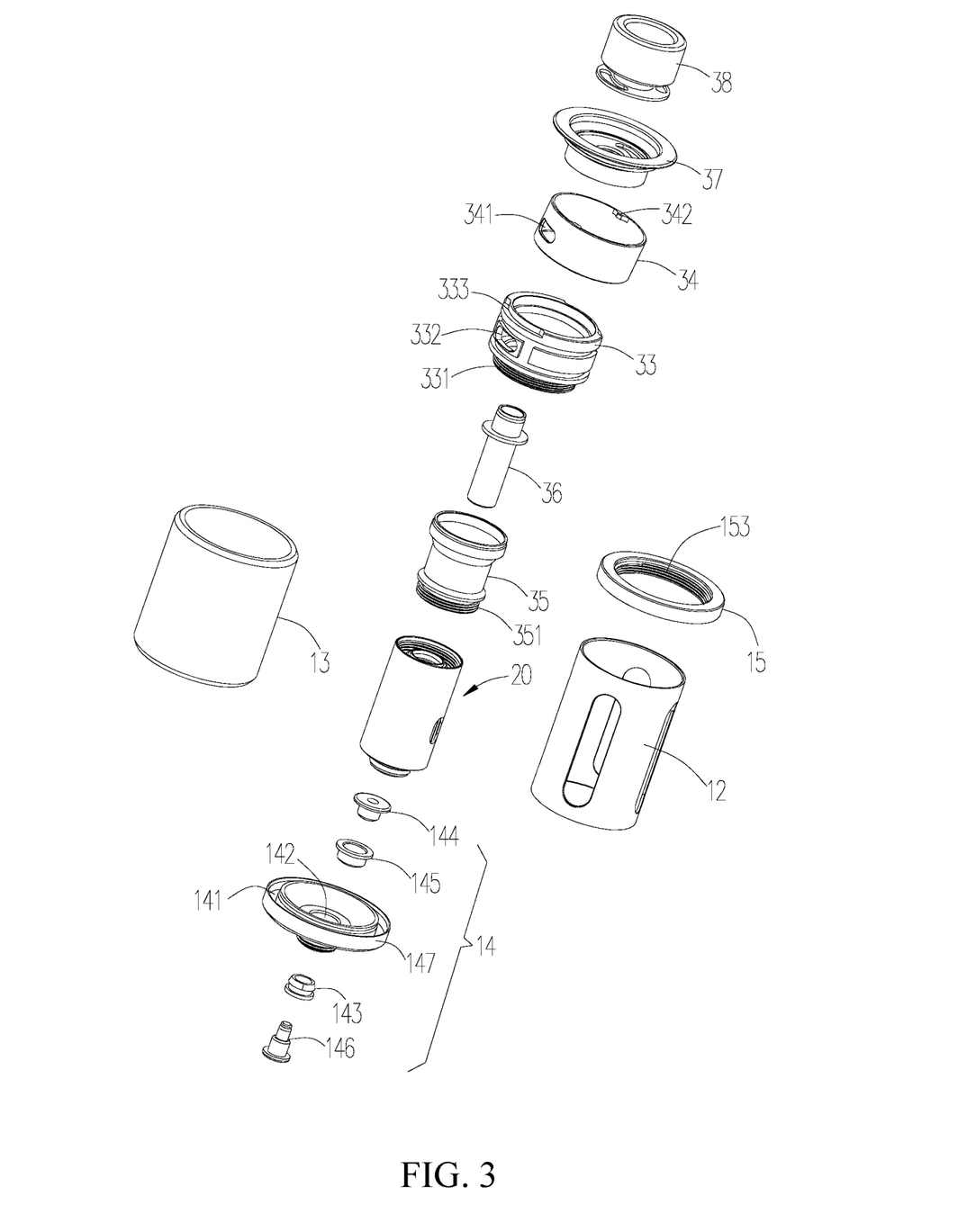
FIG. 3 is a exploded view of the atomizer of FIG. 1.

Referring to FIG. 3, the liquid storage assembly 10 includes a support housing 12, a casing 13 sleeved on the outside of the support housing 12, a base assembly 14 detachably disposed at the lower end of the support housing 12 and the casing 13, and a fixing member 15 opposite to the base assembly 14. The fixing member 15 is detachably disposed at the upper end of the support housing 12 and the casing 13.

The fixing member 15 is substantially an annular structure, the inner surface of the fixing member 15 is provided with a first inner thread 153.

The casing 13 has substantially a hollow tubular structure having openings at the upper and lower ends.

The base assembly 14 includes a base 147 and a first electrode 146, a first sealing member 143, an electrode sleeve 144 and a second sealing member 145 mounted on the base 147.

The base 147 is substantially disk-shaped, a first through hole 142 is defined in the center of the base 147. A first annular groove 141 is defined around the first through hole 142 at the edge of the upper end surface of the base 147. The first sealing member 143 and the first electrode 146 are sequentially inserted into the first through hole 142 from the lower end of the base 147, the second sealing member 145 and the electrode sleeve 144 are sequentially inserted into the first through hole 142 from the upper end of the base 147. One end of the first electrode 146 is partially received in the electrode sleeve 144 and electrically connected to the electrode sleeve 144, the opposite end of the first electrode 146 is electrically connected to the power supply device.

In the embodiment, the first sealing member 143 and the second sealing member 145 are made of rubber material. It can be understood that, the first sealing member 143 and the second sealing member 145 can also be made of silicone material to function as insulation members.

Figure 8:
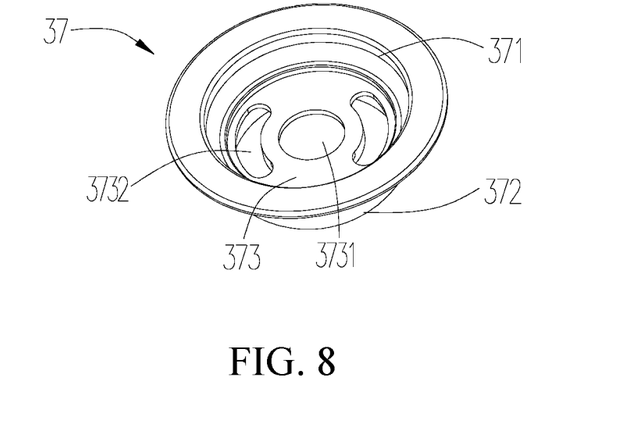
FIG. 8 is a structural view of the upper cover of the atomizer shown in FIG. 3.

Referring to FIG. 8 at the same time, a second annular groove 151 is defined on the surface of the fixing member 15 opposing to the first annular groove 141. The two opposite ends of the support housing 12 are respectively sleeved in the first annular groove 141 and the second annular groove 151. The two ends of the casing 13 sleeved on the support housing 12 are respectively tightly latched in the first annular groove 141 and second annular groove 151. In order to further improve the degree of close fitting between the casing 13 and the base assembly 14 and the degree of close fitting between the casing 13 and the fixing member 15, the upper and lower ends of the casing 13 can be sealed by a silicone gasket.

The support housing 12 may be a glass sleeve, a stainless steel sleeve, a glass-incorporated stainless steel sleeve, etc., the casing 13 is a glass sleeve. In the embodiment, the support housing 12 is a glass sleeve or a glass-incorporated stainless steel sleeve. The upper end of the casing 13 and the upper end of the support housing 12 are substantially located above the atomizing assembly 20, which is convenient for the user to observe the injection amount of the cigarette liquid through the casing 13 to achieve precise injection, and avoid excessive filling or insufficient filling of the cigarette liquid.

Figure 4:
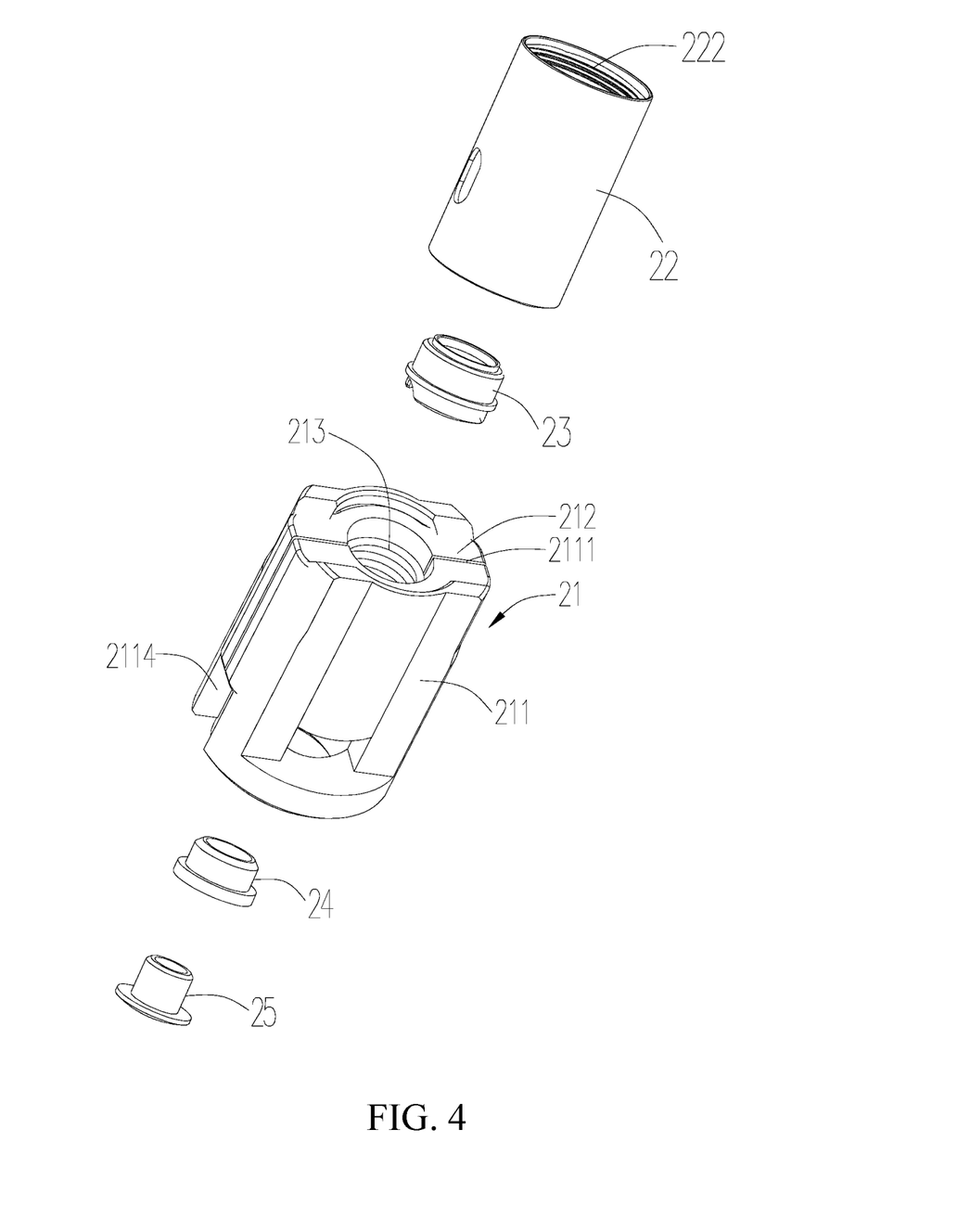
FIG. 4 is an exploded view of the atomizing assembly of the atomizer of FIG. 3.
Figure 5:
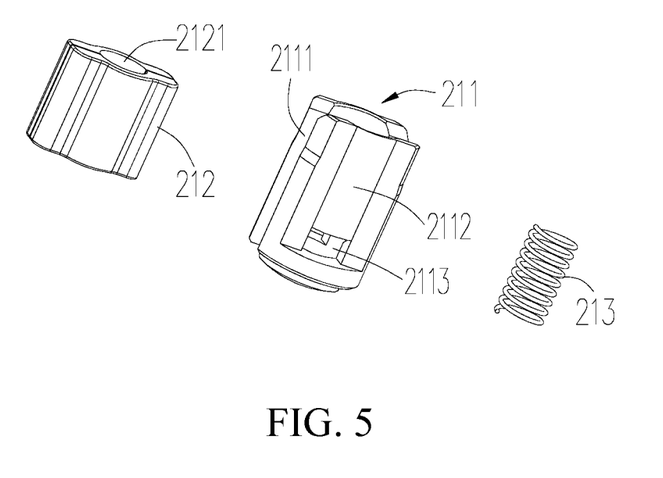
FIG. 5 is an exploded view of the atomizing head in the atomizing assembly shown in FIG. 4.

Referring to FIG. 4 and FIG. 5 simultaneously, the atomizing assembly 20 includes an atomizing head 21, an atomizing sleeve 22 sleeved on the outside of the atomizing head 21, a top cover 23 located on the top end of the atomizing head 21, and a third sealing member 24 and a second electrode 25 which are sequentially inserted into the lower end of the atomizing head 21.

Figure 6:
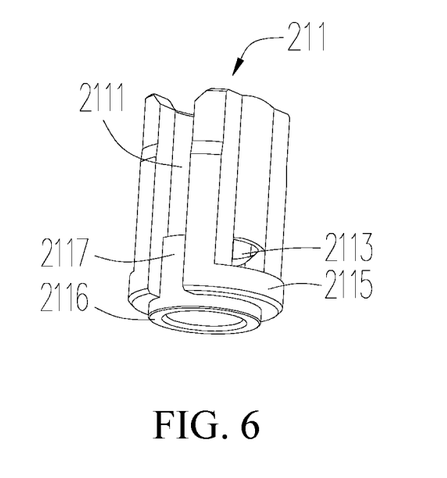
FIG. 6 is a view showing the structure of the atomizing core of the atomizing assembly shown in FIG. 5.
Figure 9:
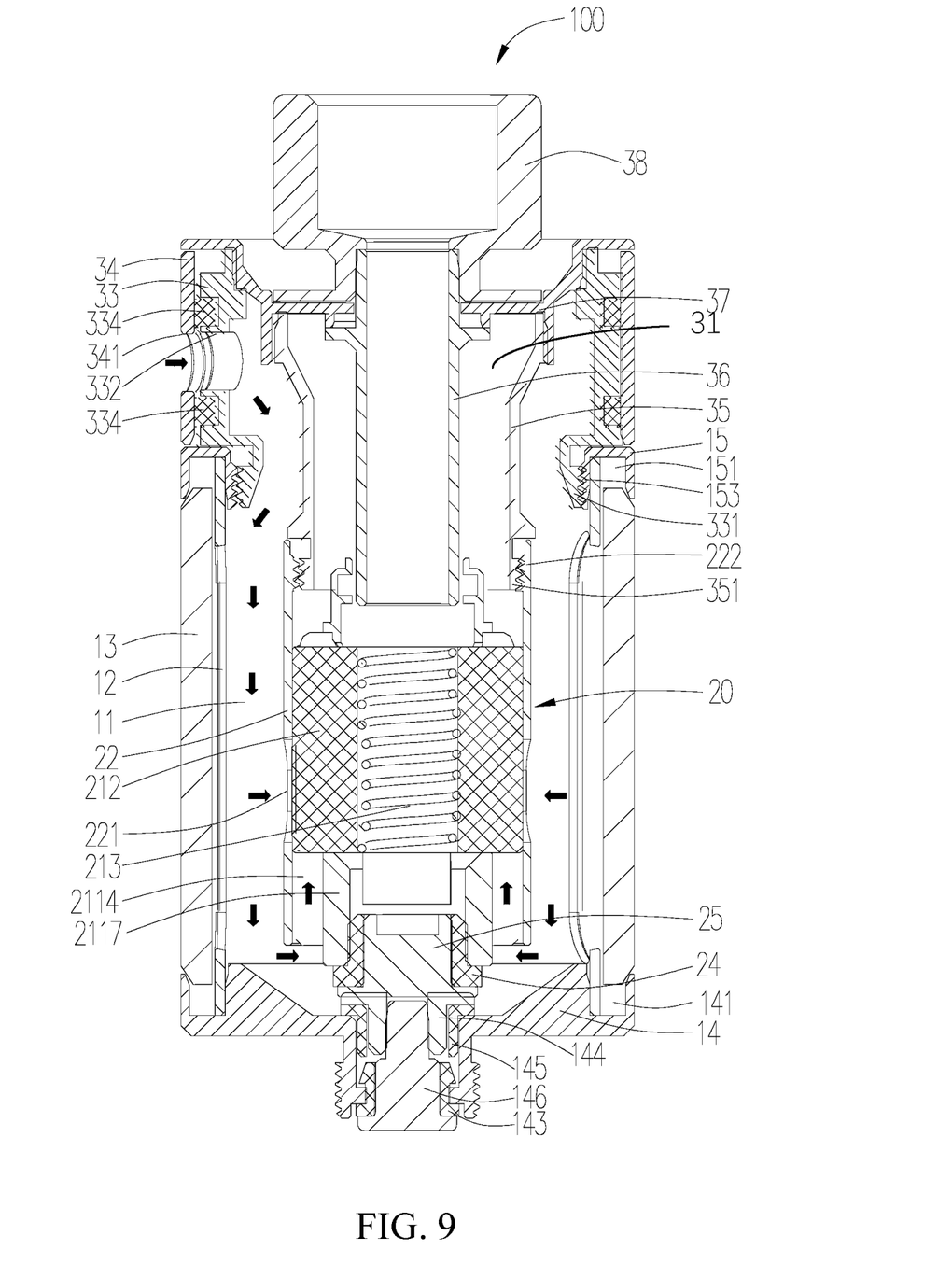
FIG. 9 is a cross-sectional view of the atomizer of FIG. 1.

Please also refer to FIG. 6 and FIG. 9, when the atomizing assembly 20 is received in the support housing 12, the cavity between the inner side wall of the support housing 12 and the outer side wall of the atomizing sleeve 22 of the atomizing assembly 20 forms a liquid storage chamber 11 for storing the cigarette liquid. The sidewall of the atomizing sleeve 22 is provided with a liquid inlet hole 221 in communication with the liquid storage chamber 11. A second inner thread 222 is defined in an upper portion of the inner surface of the atomizing sleeve 22.

The atomizing head 21 includes an atomizing core 211, a liquid absorbing member 212 embedded in the atomizing core 211, and a heating element 213 housed in the liquid absorbing member 212.

The atomizing core 211 has a substantially cylindrical structure, the atomizing core 211 includes a core 2115 and an isolation member 2116 disposed at a lower end of the inner wall of the core 2115.

The central portion of the core 2115 is provided with a recess 2111 for mounting the liquid absorbing member 212. Openings are defined on opposite sides of the recess 2111. Two air intake grooves 2112 in communication with the intake passage 31 are respectively axially defined on the outer wall of the core 2115. An air intake hole 2113 communicating with a corresponding air intake groove 2112 is defined at a lower end of the bottom of each of the air intake grooves 2112, and the air intake hole 2113 is in communication with the inside of the core 2115.

The isolation member 2116 has a substantially annular structure, the isolation member 2116 protrudes in the axial direction to form a partition portion 2117 received in the opening on both sides of the recess 2111, thereby blocking a part of the opening on both sides of the air intake groove 2112.

The liquid absorbing member 212 is located in the recess 2111 of the atomizing core 211, the lower end of the liquid absorbing member 212 abuts against the partition portion 2117. A receiving groove 2121 is defined in the center of the liquid absorbing member 212, the heating member 213 is received in the receiving groove 2121.

In other embodiments (not shown), it is understood that, the heating member 213 is wrapped outside of the liquid absorbing member 212, the liquid absorbing member 212 and the heating member 213 are disposed in the recess 2111.

Further, referring to FIG. 4, the liquid inlet hole 221 of the atomizing sleeve 22 is disposed corresponding to the recess 2111. When the atomizing sleeve 22 is sleeved on the outside of the atomizing core 211, the liquid absorbing member 212 disposed in the recess 2111 can completely cover the liquid inlet hole 221 of the atomizing sleeve 22, thereby the cigarette liquid in the liquid storage chamber 11 is allowed to pass through the liquid inlet hole 221 into the liquid absorbing member 212 and heated by the heating element 213 to generate smoke.

Further, referring to FIG. 9, the space between the inner wall of the atomizing sleeve 22 and the outer wall of the partition portion 2117 forms an auxiliary liquid inlet 2114 in communication with the inside of the core 2115. The cigarette liquid in the liquid storage chamber 11 can also enter the liquid absorbing member 212 through the auxiliary liquid inlet 2114. On the one hand, the cigarette liquid can be used efficiently; on the other hand, the cigarette liquid in the lower end of the liquid storage chamber 11 is prevented from being repeatedly heated to generate harmful substances, which may affect the health of the user.

By providing the isolation member 2116, when the cigarette liquid enters the inside of the core 2115, it must pass through the liquid absorbing member 212, so that the cigarette liquid in the liquid storage chamber 11 is prevented from directly entering the air intake hole 2113, achieve separation of air inlet and liquid inlet.

Referring to FIG. 4, the top cover 23 is a hollow structure having an opening at each of two ends. The top cover 23 is disposed at the top end of the atomizing core 211, the third sealing member 24 and the second electrode 25 are sequentially inserted into bottom end of the atomizing core 211. One end of the second electrode 25 is mounted on the isolation member 2116 and electrically connected to the heating element 213, the other end of the second electrode 25 is electrically connected to the first electrode 146.

In the embodiment, the third sealing member 24 is made of rubber material. It can be understood that, the third sealing member 24 can also be made of silicone material to function as an insulation member.

In the embodiment, the liquid absorbing member 212 may be made one or a combination of at least two of cotton, porous ceramic and metal foam.

Alternatively, the heating member 213 of the embodiment is a spiral heating wire having a substantially cylindrical structure, and is not limited thereto. The heating element 213 may also be a heating plate or a heating tube, any component or device that is disposed in the liquid absorbing member 212 and capable of atomizing the cigarette liquid is within the scope of the present invention.

Referring to FIG. 3, the adjustment assembly 30 includes an upper cover inner ring 33, an adjustment member 34, an upper cover connector 35, a vent tube 36, an upper cover 37, and a mouthpiece connector 38. The adjustment member 34 is rotatably sleeved on the upper cover inner ring 33. The upper cover 37 is received in the upper cover inner ring 33, one end of the upper cover 37 is connected to the upper cover inner ring 33, the opposite end of the upper cover 37 is connected with the upper cover connector 35. The vent tube 36 is received in the interior of the upper cover connector 35. One end of the vent tube 36 extends through the upper cover 37 and then is detachably connected to the mouthpiece connector 38. The mouthpiece connector 38 is rotatably connected to the upper cover 37. The specific structure of the upper cover inner ring 33, the adjustment member 34, the upper cover connector 35, the vent tube 36, the upper cover 37, and the mouthpiece connector 38 will be described later.

The upper cover inner ring 33 has an annular structure having an opening at both ends each of two ends, the lower end of the upper cover inner ring 33 is provided with a first outer thread 331 engaging with the first inner thread 153. A first liquid injection hole 332 in communication with the liquid storage chamber 11 is disposed on the side wall of the upper cover inner ring 33, the upper cover inner ring 33 is further provided with a positioning groove 333 having an annular structure.

The adjustment member 34 has an annular structure with an opening at each of two ends, a second liquid injection hole 341 is defined in the sidewall of the adjustment member 34 corresponding to the first liquid injection hole 332. The inner sidewall of the adjustment member 34 is provided with a positioning block 342 corresponding the positioning groove 333. When the adjustment member 34 is sleeved on the outside of the upper cover inner ring 33, the positioning block 342 is located in the positioning groove 333.

Rotating the adjustment member 34, when the positioning block 342 of the adjustment member 34 is rotated to one end of the positioning groove 333, the second liquid injection hole 341 of the adjustment member 34 is completely in communication with the first liquid injection hole 332 of the upper cover inner ring 33; at this time, the user can add the cigarette liquid into the liquid storage chamber 11. On the contrary, rotating the adjustment member 34, when the positioning block 342 is rotated to the opposite end of the positioning groove 333, the first liquid injection hole 332 is completely shielded by the inner wall of the adjustment member 34. At this time, the second liquid injection hole 341 is not in communication with the first liquid injection hole 332, and the user cannot add the cigarette liquid into the liquid storage chamber 11.

Referring to FIG. 9, the second liquid injection hole 341 is partially or completely in communication with the first liquid injection hole 332 of the upper cover inner ring 33 by rotating the adjustment member 34, the cigarette liquid is injected into the liquid storage chamber 11 through the second liquid injection hole 341 and the first liquid filling hole 332. The cigarette liquid passes through the liquid inlet hole 221 of the atomizing sleeve 22 and the bottom of the atomizing core 211, and then absorbed by the liquid absorbing member 212; thereby the cigarette liquid is heated and atomized by the heating element 213. The direction indicated by the arrow in FIG. 9 is the flow direction of the cigarette liquid from the injecting to the atomization process.

Further, a fourth sealing member 334 is further disposed on the sidewall of the upper cover inner ring 33. During the rotation of the adjustment member 34, the fourth sealing member 334 can always resist the inner wall of the adjustment member 34, thereby enhancing the feel of the rotation and the user's experience, at the same time, the fourth sealing member 334 also acts as a sealing member to prevent the leakage of the cigarette liquid.

Figure 10:
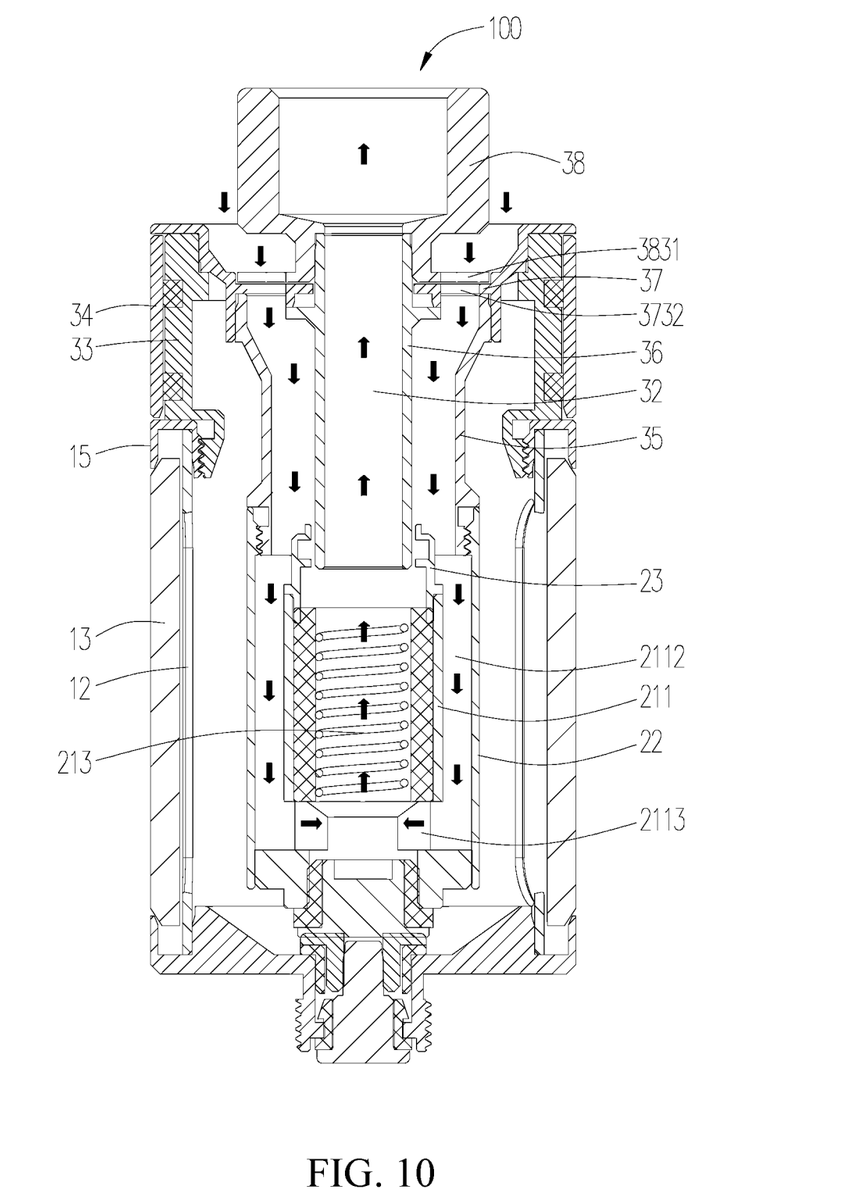

Referring to FIG. 10, the inner cavity of the vent tube 36 forms an outlet passage 32, an end of the vent tube 36 away from the mouthpiece connector 38 is partially received in the above-mentioned top cover 23, and the outer wall of the vent tube 36 is connected to the upper cover 37. The cavity between the outer wall of the vent tube 36 and the inner wall of the upper cover connector 35 forms an intake passage 31, the intake passage 31 is in communication with the air intake groove 2112 of the atomizing assembly 20, the outside air of the electronic cigarette can enter the air intake groove 2112 via the intake passage 31.

Referring to FIG. 9, a second outer thread 351 engages with the second inner thread 222 is defined at one end of the upper cover connector 35, which ensures the tightness of the liquid storage chamber 11 and prevents the leakage of the cigarette liquid into the intake passage 31. Referring to FIG. 8, the upper cover 37 includes an upper connector 371, a lower connector 372 provided at a lower end of the upper connector 371, and a first connecting member 373 provided at an intersection of the upper connector 371 and the lower connector 372. The upper connector 371 has a tubular structure, the lower connector 372 has a cylindrical structure, the upper connector 371 is tightly fitted with the inner wall of the upper cover inner ring 33, the lower connector 372 is tightly fitted with the upper end of the upper cover connector 35. A third through hole 3731 is disposed at a center of the first connecting member 373, the vent tube 36 is capable of passing through the third through hole 3731. The first connecting member 373 is further provided with at least one first air inlet hole 3732. At least one first air inlet hole 3732 is further defined at an edge of the first connecting member 373, the first air inlet hole 3732 is in communication with the intake passage 31.

Figure 7:
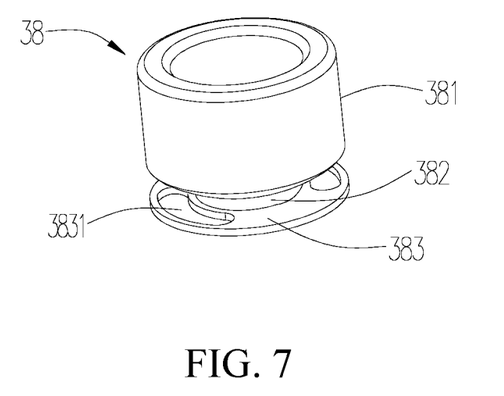
FIG. 7 is a structural view of the mouthpiece connector of the atomizer shown in FIG. 3.

Referring to FIG. 7, the mouthpiece connector 38 includes a main body 381, a connecting tube 382 disposed at a lower end of the main body 381 and in communication with the main body 381, and a second connecting member 383 extending radially outwardly from a lower end of the connecting tube 382. One end of the vent tube 36 is tightly connected to the connecting tube 382, the second connecting member 383 is received in the upper connector 371 of the upper cover 37, and the second connecting member 383 is provided with at least one second air inlet hole 3831 corresponding to the first air inlet hole 3732. When the second air inlet hole 3831 is at least partially overlapped with the first air inlet hole 3732 by rotating the mouthpiece connector 38, the first air inlet hole 3732 and the second air inlet hole 3831 are in communication with each other. It can be understood that the user can directly inhale through the mouthpiece connector 38 or to mount a communication member having an opening at each of two ends on the mouthpiece connector 38, through which the user can also inhale.

Referring to FIG. 9 and FIG. 10, when the user inhales, the external air enters the intake passage 31 via the second air inlet hole 3831 and the first air inlet hole 3732 located at the top of the electronic cigarette, and then, flows into the atomizing core 211 through the air intake groove 2112 and the air intake hole 2113 in the side wall of the atomizing core 211, mixes with the smoke in the atomizing core 211, and finally the mixture flows out through the outlet passage 32 of the vent tube 36 for the user to inhales. The direction of the arrow in FIG. 10 is the flow direction of the airflow. In the embodiment, the air intake hole 2113 is defined on the side wall of the atomizing core 211, which prevents the excess cigarette liquid from leaking from the air intake hole 2113 when the liquid absorbing member 212 is saturated, thereby the air intake hole 2113 is not easy to be polluted, the atomizer or the electronic cigarette has a simple structure and is easy to use.

When the atomizer or the electronic cigarette provided by the present disclosure is used, the user can control the amount of intake air entering the interior of the electronic cigarette by adjusting the overlapping area of the first air inlet hole 3732 and the second air inlet hole 3831, and the adjustment operation is more convenient.

The above-mentioned embodiments merely represent several implementations of the present application, and the descriptions thereof are more specific and detailed, but they shall not be understood as a limitation on the scope of the present application. It should be noted that, for those of ordinary skill in the art, variations and improvements may still be made without departing from the concept of the present application, and all of which shall fall into the protection scope of the present application. Therefore, the scope of protection of the present application shall be subject to the appended claims.

What is claimed is:

1. An atomizer, comprising:
a liquid storage assembly;
an adjustment assembly detachably mounted at one end of the liquid storage assembly; and
an atomizing assembly received in the liquid storage assembly;
wherein the adjustment assembly is defined with an intake passage therein, the atomizing assembly comprises an atomizing head, the atomizing head comprises an atomizing core, at least one air intake groove in communication with the intake passage is defined on an outer surface of a side wall of the atomizing core, an air intake hole communicating with a corresponding air intake groove is defined at a lower end of a bottom of each of the air intake groove;
wherein the atomizing core is provided with a recess, openings are defined on opposite sides of the recess, the atomizer head further comprises a liquid absorbing member and a heating element, the liquid absorbing member wraps the heating element or the heating element wraps the liquid absorbing member, the liquid absorbing member and the heating element are located in the recess, wherein the atomizing core comprises a core and an isolation member disposed at a lower end of an inner wall of the core, the recess is defined on the core, the isolation member protrudes in an axial direction to form a partition portion received in the openings on opposite sides of the recess, a lower end of the liquid absorbing member abuts against the partition portion.

2. The atomizer according to claim 1, wherein the adjustment assembly comprises an upper cover and a mouthpiece connector rotatably mounted on the upper cover, the upper cover is provided with at least one first air inlet hole, the mouthpiece connector is provided with at least one second air inlet hole corresponding to the first air inlet hole, the first air inlet hole is in communication with the intake passage; when the second air inlet hole is at least partially overlapped with the first air inlet hole by rotating the mouthpiece connector, the second air inlet hole is in communication with the intake passage through the first air inlet hole.

3. The atomizer according to claim 2, wherein the atomizing assembly further comprises an atomizing sleeve sleeved on the outside of the atomizing head, the adjustment assembly further comprise an upper cover connector and a vent tube received in the upper cover connector, one end of the upper cover connector is detachably connected to the atomizing sleeve, the other end of the upper cover connector is connected to the upper cover, one end of the vent tube is connected to and in communication with the mouthpiece connector, the other end of the vent tube is in communication with the inside of the atomizing core.

4. The atomizer according to claim 3, wherein the atomizing assembly comprises a top cover mounted on a top end of the atomizing core, the top cover is a hollow structure having an opening at each of two ends, one end of the vent pipe away from the mouthpiece connector is received in the top cover.

5. The atomizer according to claim 3, wherein a cavity between an outer wall of the vent pipe and an inner wall of the upper cover connector forms the intake passage.

6. The atomizer according to claim 3, wherein a sidewall of the atomizing sleeve is provided with at least one liquid inlet hole, the liquid inlet hole can be completely covered by the liquid absorbing member.

7. The atomizer according to claim 6, wherein the adjusting assembly further comprises an upper cover inner ring sleeved on the upper cover connector and an adjusting member rotatably sleeved on the upper cover inner ring, a first liquid injection hole is defined on the upper cover inner ring, a second liquid injection hole is defined on the adjusting member corresponding to the first liquid injection hole, rotating the adjustment member can enable the second liquid injection hole to communicate with the first liquid injection hole.

8. The atomizer according to claim 7, wherein the liquid storage assembly further comprises a support housing, a casing sleeved on the support housing, a base assembly detachably disposed at a lower end of the support housing and a lower end of the casing, and a fixing member opposite to the base assembly and detachably disposed at an upper end of the support housing and an upper end of the casing, the fixing member is detachably connected to the upper cover inner ring.

9. The atomizer according to claim 8, wherein a cavity among an outer side wall of the upper cover connector, an outer side wall of the atomizing sleeve, an inner side wall of the upper cover inner ring and an inner side wall of the support housing from a liquid storage chamber communicating with the first liquid injection hole, the cigarette liquid in the liquid storage chamber can pass through the liquid inlet hole of the atomizing sleeve into the liquid absorbing member.

10. The atomizer according to claim 9, wherein a space between an inner wall of the atomizing sleeve and an outer wall of the partition portion forms an auxiliary liquid inlet in communication with the inside of the core, the cigarette liquid in the liquid storage chamber can pass through the auxiliary liquid inlet into the liquid absorbing member.

11. An electronic cigarette, comprising:
an atomizer, comprises:
a liquid storage assembly;
an adjustment assembly detachably mounted at one end of the liquid storage assembly; and
an atomizing assembly received in the liquid storage assembly, wherein the adjustment assembly is defined with an intake passage therein, the atomizing assembly comprises an atomizing head, the atomizing head comprises an atomizing core, at least one air intake groove in communication with the intake passage is defined on an outer surface of a side wall of the atomizing core, an air intake hole communicating with a corresponding air intake groove is defined at a lower end of a bottom of each of the air intake groove;
wherein the atomizing core is provided with a recess, openings are defined on opposite sides of the recess, the atomizer head further comprises a liquid absorbing member and a heating element, the liquid absorbing member and the heating element or the heating element wraps the liquid absorbing member, the liquid absorbing member and the heating element are located in the recess, wherein the atomizing core comprises a core and an isolation member disposed at a lower end of an inner wall of the core, the recess is defined on the core, the isolation member protrudes in an axial direction to form a partition portion received in the openings on opposite sides of the recess, a lower end of the liquid absorbing member abuts against the partition portion.

12. The electronic cigarette according to claim 11, wherein the adjustment assembly comprises an upper cover and a mouthpiece connector rotatably mounted on the upper cover, the upper cover is provided with at least one first air inlet hole, the mouthpiece connector is provided with at least one second air inlet hole corresponding to the first air inlet hole, the first air inlet hole is in communication with the intake passage; when the second air inlet hole is at least partially overlapped with the first air inlet hole by rotating the mouthpiece connector, the second air inlet hole is in communication with the intake passage through the first air inlet hole.

13. The electronic cigarette according to claim 12, wherein the atomizing assembly further comprises an atomizing sleeve sleeved on the outside of the atomizing head, the adjustment assembly further comprise an upper cover connector and a vent tube received in the upper cover connector, one end of the upper cover connector is detachably connected to the atomizing sleeve, the other end of the upper cover connector is connected to the upper cover, one end of the vent tube is connected to and in communication with the mouthpiece connector, the other end of the vent tube is in communication with the inside of the atomizing core.

14. The electronic cigarette according to claim 13, wherein the atomizing assembly comprises a top cover mounted on a top end of the atomizing core, the top cover is a hollow structure having an opening at each of two ends, one end of the vent pipe away from the mouthpiece connector is received in the top cover.

15. The electronic cigarette according to claim 13, wherein a cavity between an outer wall of the vent pipe and an inner wall of the upper cover connector forms the intake passage.

16. The electronic cigarette according to claim 13, wherein a sidewall of the atomizing sleeve is provided with at least one liquid inlet hole, the liquid inlet hole can be completely covered by the liquid absorbing member.

* * * * *